United States Patent [19]

Bryant et al.

[11] Patent Number: 5,446,061
[45] Date of Patent: Aug. 29, 1995

[54] METHODS FOR LOWERING SERUM CHOLESTEROL

[75] Inventors: Henry U. Bryant; Timothy A. Grese, both of Indianapolis, Ind.

[73] Assignee: Eli Lilly and Company, Indianapolis, Ind.

[21] Appl. No.: 148,038

[22] Filed: Nov. 5, 1993

[51] Int. Cl.$^6$ .............................................. A61K 31/35
[52] U.S. Cl. ...................................................... 514/456
[58] Field of Search ........................................ 514/456

[56] References Cited

U.S. PATENT DOCUMENTS 5,254,568 10/1993 Kapil et al. ..................... 514/320

FOREIGN PATENT DOCUMENTS

0470310A1 2/1992 European Pat. Off. .
WO93/10741 12/1992 WIPO .

OTHER PUBLICATIONS

CA 113: 231155x (1990).
Sreenivasulu, S., et al., "studies on competition to estrogen binding sites in the immature rat uterus," *Indian J. Exp. Biol.*, 30(12), 1115–17, (Dec. 1992).
Sreenivasulu, S., et al., "Duration of antiestrogenecity of compound CdRI-85/287: a new orally active nonsteroidal antiimplantation agent," *Indian J. Exp. Biol.*, 30(11), 968–71, (Nov. 1992).
Sreenivasulu, S., et al., "CDRI-85/287, a novel antiestrogen and antiimplantation agent: biological profile and interaction with the estrogen receptors in immature rat uterus," *Contraception*, 45(1), 81–92, (Jan 1992).
Dhar, J. D., et al., "Biological profile of 2-[4-(-2-N-piperidinoethoxy)phenyl]-3-phenyl (2H) benzo(B)pyran-a potent antiimplantation agent in rats," *Contraception*, 44(4), 461–72, (Oct. 1991).
Saeed, A., et al. "Structure-activity relationship of antiestrogens, studies on 2, 3-diaryl-1-benzopyrans" *J. Med. Chem.*, 33 (12), 3210–16, (1990).
Sharma, A. P., et al., "Structure-activity relationship of antiestrogens, effect of the side chain and its position on activity of 2,3-diary-2H-1-benzopyrans" *J. Med. Chem.*, 33(12), 3216–22, (1990).
Sharma, A. P., et al., "Structure-activity relationship of antiestrogens. Phenolic analogs of 2,3-diarly-2-H-1-benzopyrans," *J. Med. Chem.*, 33(12), 3222–9, (1990).
Dhar, J. D., et al., "Biological profile of 2-[4-(-2-N-piperidinoethoxy) phenyl]-3-phenyl (2H) benzo(b) pyran," *Contraception* 45(4), 397–398, (1990).
Verm et al., "Synthesis of 3-aryl-1-(4-methoxy phenyl)-2-[4-(2-substituted aminoethoxy) phenyl]-L-propen-1-ones and benzopyran derivative," *Indian J. of Chem.*, 32B, 239–243 (Feb. 1993).

Primary Examiner—Raymond Henley, III
Assistant Examiner—K. Weddington
Attorney, Agent, or Firm—James J. Sales; Gerald V. Dahling

[57] ABSTRACT

A method of lowering serum cholesterol levels, comprising administering an effective amount of a compound having the formula

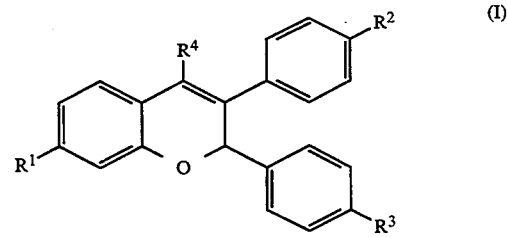

wherein:

$R^1$ and $R^2$ are, independently, —H, —OH, halo, —OC$_1$–C$_{17}$ alkyl, —OC$_3$–C$_6$ cycloalkyl, —O(CO)C$_1$–C$_{17}$ alkyl, —O(CO) aryl, —O(CO)O aryl, or —OSO$_2$-(n-butyl or n-pentyl);

$R^3$ is

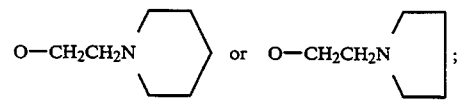

and $R^4$ is —H, methyl, ethyl, propyl, ethenyl or ethynyl; or a pharmaceutically acceptable salt or solvate thereof, to an animal in need of lower cholesterol levels.

19 Claims, 3 Drawing Sheets

METHODS FOR LOWERING SERUM CHOLESTEROL

BACKGROUND OF THE INVENTION

The present invention relates to the discovery that a group of 2-phenyl-3-aryl-dihydrobenzopyrans are useful for lowering serum cholesterol.

All mammalian cells require cholesterol as a structural component of their cell membranes and for non-sterol end products. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins (LDL'S) have been demonstrated to be a major contributing factor in the development and progression of atherosclerosis.

Estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience unacceptable bleeding. Furthermore, combining progesterone with estrogen seems to blunt the serum cholesterol lowering effects of estrogen. The significant undesirable effects associated with estrogen therapy support the need to develop alternative therapies for hypercholesterolemia that have the desirable effect on serum LDL but do not cause undesirable effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect and are subject to the same adverse effects associated with estrogen therapy.

The current invention provides methods for lowering serum LDL levels without the associated adverse effects of estrogen therapy, and thus provides an effective and acceptable treatment for hypercholesterolemia.

SUMMARY OF THE INVENTION

This invention provides new methods for lowering serum cholesterol levels, comprising administering a compound of formula (I):

wherein:

$R^1$ and $R^2$ are, independently, —H, —OH, halo, —OC$_1$-C$_{17}$ alkyl, —OC$_3$-C$_6$ cycloalkyl, —O(CO)C$_1$-C$_{17}$ alkyl, —O(CO) aryl, —O(CO)O aryl, or —OSO$_2$-(n-butyl or n-pentyl);

$R^3$ is and $R^4$ is —H, methyl, ethyl, propyl, ethenyl or ethynyl or a pharmaceutically acceptable salt or solvate thereof, to an animal in need of lower serum cholesterol levels.

DETAILED DESCRIPTION OF THE INVENTION

The general chemical terms used in the description of a compound of formula I have their usual meanings. For example, the term "alkyl" by itself or as part of another substituent means a straight or branched chain alkyl radical having the stated number of carbon atoms, such as methyl, ethyl, propyl and isopropyl, and higher homologs and isomers where indicated.

The term "cycloalkyl" means a cyclic alkyl radical having the stated number of carbon atoms. Examples of cycloalkyl groups are cyclopropyl, cyclopentyl and cyclohexyl.

The term "aryl" includes groups such as phenyl, naphthyl, thienyl or furyl, each of which may be unsubstituted or monosubstituted with a group selected from hydroxyl, halo, C$_1$-C$_3$ alkyl, or C$_1$-C$_3$ alkoxy.

The term "halo" means chloro, fluoro, bromo or iodo.

Specific examples of the compounds of formula I include the following:

Compound 1

2-[4-[2-(1-piperidino)ethoxy]phenyl]-3-(4-hydroxyphenyl)-7-hydroxy-2H-1-benzopyran Compound 2

2-[4-[2-(1-piperidino)ethoxy]phenyl]-3-(4-hydroxyphenyl) -2H-1-benzopyran

Compound 3

2-[4-[2-(1-piperidino)ethoxy]phenyl]-3-phenyl-7-methoxy-2H-1-benzopyran

Compound 4

2-[4-[2-(1-pyrrolidino)ethoxy]phenyl]-3-(4-hydroxyphenyl)-7-hydroxy-2H-1-benzopyran Compound 5

2-[4-[2-(1-piperidino)ethoxy]phenyl]-3-(4-hydroxyphenyl) -4-methyl-7-hydroxy-2H-1-benzopyran The current invention concerns the discovery that the compounds of formula I are useful for lowering serum cholesterol. The methods of treatment provided by this invention can be practiced by administering to an animal an amount that lowers serum cholesterol of a compound of formula I, or a pharmaceutically acceptable salt or solvate thereof. The methods include both medical therapeutic and/or prophylactic treatment, as appropriate. Generally, the formula I compound is formulated with common excipients, diluents or carriers, and put into capsules or compressed into tablets, or formulated as elixirs or solutions for convenient oral administration, or administered by the intramuscular or intravenous routes. The compounds may also be administered transdermally.

The methods of this invention also include the administration of a compound of formula I together with estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources—Ayerst), and the like.

All of the compounds used in the methods of the current invention can be made according to established or analogous procedures, such as those detailed in European Patent Application No. 0 470 310 A1 and PCT Application WO 93/10741. Modifications to these methods may be necessary to accommodate reactive functionalities of particular substituents. Such modifications would be either apparent to, or readily ascertained by, those skilled in the art.

Thus, the compounds of formula I in which $R^4$ is H can be manufactured, for example, by reacting a compound of formula II:

in which $R^5$ and $R^6$ are $R^1$ and $R^2$, respectively, or a protected hydroxyl group, with 4-hydroxybenzaldehyde to produce a compound of formula III:

2) forming a compound of formula IV:

3) reacting this compound with a compound of formula V:

in which X is a halide, to form a compound of formula VI:

and, if necessary, 4) deprotecting and acylating or alkylating $R^5$ and $R^6$

Alternatively, the compounds of formula I in which $R^4$ is not H can be manufactured, for example, by reacting a compound of formula II in which $R^5$ and $R^6$ are $R^1$ and $R^2$, respectively, or a protected hydroxyl group, with 4-hydroxybenzaldehyde to produce a compound of formula VIII:

2) reacting this compound with a compound of formula V in which X is a halide to form a compound of formula X:

3) reacting this compound with a Grignard reagent of formula $R^4MgX$ in which X is a halide to form a compound of formula XI:

4) dehydrating compound XI to form a compound of formula XII:

and, if necessary, 5) deprotecting and acylating or alkylating $R^5$ and $R^6$.

When producing the formula I compounds wherein $R^1$ is H, preferably in the above processes $R^5$ is H and $R^6$ is a protected hydroxy group.

When the processes are used to produce a formula I compound in which $R^1$ and $R^2$ are each alkoxy or carboxy, then $R^5$ and $R^6$ may be $R^1$ and $R^2$, respectively, or may each be in the form of a protected hydroxy group. If $R^1$ or $R^2$ is a hydroxy group, then $R^5$ or $R^6$, respectively, in the above process is preferably in the form of a protected hydroxy group. If $R^5$ or $R^6$ is a protected group, then preferably the protecting group is 3,4-dihydropyran. The 3,4-hydropyran may be reacted with a compound of formula IX:

where one of $R^7$ and $R^8$ is a hydroxy group and the other is hydrogen or a hydroxy group or an alkoxy or carboxy group, to form a tetrahydropyranyl ether. Preferably the reaction is carried out in the presence of a sulphonic acid, such as para-toluene sulphonic acid or the like in an ether solvent, such as dioxan or the like.

The reaction may be effected for a period of up to 4 hours; and the crude reaction product, after stipulated processing, may be purified, e.g., by crystallization from a petroleum solvent such as hexane or by rapid chromatography over silica gel.

The reaction of the compound of formula II with the 4-hydroxybenzaldehyde may be effected in the presence of a cyclic or open chain secondary and/or tertiary amino base such as piperidine or triethyl amine, and an aromatic hydrocarbon solvent such as benzene or the like. The solvent may be added at periodic intervals to replenish its loss during the reaction. This reaction may be effected for a period of about 30 hours. Thereafter, the reaction mixture may be cooled and washed with water, the organic layer separated, dried over $Na_2SO_4$ and concentrated. The solidified material may be filtered off, washed with a halogenated solvent such as chloroform, methylene dichloride or the like to give a compound of formula III. Generally, compound III will be produced as a mixture with a compound of formula VIII:

For example, the product mixture may contain a ratio of compound VIII to compound III of 1.0:1.5. The filtrate containing compounds III and VIII may be concentrated, chromatographed and eluted with an eluate of increasing polarity, such as ethyl acetate in hexane or the like, thereby separating out the compound of formula III.

The compound of the formula III may be converted to a compound of formula IV by reduction, for example by treating with a hydride such as sodium borohydride or the like in an alcoholic solvent such as ethyl alcohol or the like. Cyclodehydration may also be carried out; typically, work-up of the product, e.g., thermal work-up, may cause cyclodehydration. The hydride may be added in different proportions, at intervals of 10 to 15 minutes, at room temperature under stirring. The reaction may be continued for a period of up to 12 to 15 hours. The reaction product, after concentration, pH adjustment and extraction with a polar solvent such as ethyl acetate, is purified by chromatography, e.g., flash chromatography over silica gel to yield a compound of formula IV.

The compound of formula IV can be treated with an appropriate heterocyclic alkyl halide, e.g., a piperidino- or pyrrolidinoalkyl halide, preferably in the presence of a basic catalyst such as potassium carbonate and a suitable ketonic solvent such as acetone or the like. This reaction may be followed by purification by chromatography, e.g., on alumina using hexane or a mixture thereof with a polar solvent to yield a compound of formula VI.

If $R^5$ and $R^6$ are not protected hydroxy groups, then the compound produced is a compound of formula I. If $R^5$ or $R^6$ is a protected hydroxy group, then the protecting group(s) may be removed by known methods, e.g., by use of an acid such as hydrochloric acid in an alcoholic solvent such as ethanol. The deprotected hydroxy group(s) may, if desired, be alkylated or acylated by known methods to give other compounds of formula I.

Alternatively, the compound of formula III can be converted to the compound of formula VIII by heating with sodium acetate in methanol.

The compound of formula VIII can be treated with an appropriate heterocyclic alkyl halide, e.g., a piperidino- or pyrrolidinoalkyl halide preferably in the presence of a basic catalyst such as potassium carbonate and a suitable ketonic solvent such as acetone or the like. This reaction may be followed by purification by chromatography, e.g., on silica gel using a mixture of hexane and a polar solvent containing a small amount of triethylamine or ammonium hydroxide, to yield a compound of formula X.

The compound of formula X can be treated with an appropriate Grignard reagent, e.g., methylmagnesium bromide or ethylmagnesium bromide, in diethyl ether or a tetrahydrofuran at 0° C. This reaction may be followed by purification by chromatography, e.g., on silica gel using a polar solvent such as ethyl acetate or acetone or a mixture thereof, to yield a compound of formula XI.

The compound of formula XI can be dehydrated by treating with acetic acid and water at 100° C. for 10 min. This reaction may be followed by purification by chromatography, e.g., on silica gel using a polar solvent such as ethyl acetate or acetone or a mixture thereof, to give a compound of formula XII.

When $R^5$ and $R^6$ are not protected hydroxy groups, then the compound produced is a compound of formula I. If $R^5$ and $R^6$ are hydroxy group(s) protected as the tetrahydropyranyl ether(s) they are also deprotected in this reaction to yield a compound of formula I in which $R^1$ and $R^2$ are hydroxy. The deprotected hydroxy group(s) may, if desired, by alkylated or acylated by known methods to give other compound of formula I.

The unprotected starting compound of formula (II)':

where $R^1$ and $R^2$ are as defined supra can be prepared by methods known in the art. For example, when $R^1$ is H and $R^2$ is OH, it can be prepared by condensation of phenol with 4-methoxy-phenylacetyl chloride (in turn prepared from 4-methoxy-phenylacetic acid) to afford an ester which on typical Fries rearrangement in the presence of anhydrous aluminum chloride yields a mixture which can be resolved chromatographically to afford the desired starting material that can be characterized by its physical and spectral data.

When $R^1$ is, e.g., methoxy and $R^2$ is as defined supra, the starting compound II' may be prepared by Friedel-Crafts acylation of a corresponding phenol, such as 3-methoxyphenol or the like, with a suitable substituted or unsubstituted phenylacetyl chloride, using a catalyst, such as anhydrous aluminum chloride. The resultant product may be purified by steam distillation and/or column chromatography.

In turn, when $R^1$ and $R^2$ are both OH, the starting compound can be prepared by Friedel-Crafts acylation of resorcinol with 4-methoxyphenyl acetyl chloride. This reaction affords a mixture of trihydroxydeoxybenzoin and methoxy dihydroxydeoxybenzoin. The latter compound may be converted into the desired trihydroxy compound by heating it with anhydrous pyridine hydrochloride.

The formula I compounds can form pharmaceutically acceptable acid and base addition salts with a variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthatene-2-benzoate, bromide, isobutyrate, phenylbutyrate, β-hydroxybutyrate, butyne-1,4-dioate, hexyne-1,4-dioate, caprate, capDilate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

In addition, some of the formula I compounds may form solvates with water or organic solvents such as ethanol. These solvates are also contemplated for use in the methods of this invention.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the formula I compounds, either alone or in combination with estrogen, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The formula I compounds, either alone or in combination with estrogen, can also be formulated as elixirs or solutions for convenient oral administration or as solutions appropriate for parenteral administration, for instance by intramuscular, subcutaneous or intravenous routes. Additionally, the compounds, either alone or in combination with estrogen, can be formulated as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to lower serum cholesterol according to this invention will depend upon the severity of the condition, the route of administration, and related factors. In humans, generally accepted and effective daily doses will be from about 0.1 to about 1000 mg, and more typically from about 50 to about 600 mg. Such dosages will be administered to the patient from once to about three times each day, or more often as needed to lower serum cholesterol effectively.

If estrogen is also administered, generally accepted and effective daily doses of estrogen will be from about 0.01 to about 4.0 mg, and more typically from about 0.1 to about 2.0 mg. These doses are also administered to the patient from once to about three times a day, or more often as needed.

A preferred formula I compound of this invention is the compound wherein
$R^1$ is H or OH;
$R^2$ is OH;
$R^3$ is and
$R^4$ is H or methyl.

It is usually preferable to administer the formula I compound in the form of an acid addition salt, as is customary in the administration of pharmaceuticals bearing a basic group, such as the piperidino ring. It is also advantageous to administer the compound orally.

A preferred group of animals are human patients, and a particularly important group of patients are aging humans (e.g., post-menopausal females).

For the purposes of this invention, the following are typical oral dosage forms. In these examples, "Active ingredient" means a compound of formula 1.

Capsules

Formulation 1

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Tablets

The components in Formulation I can be blended and compressed to form tablets.

Alternatively, tablets each containing 0.1–1000 mg of active ingredient are made up as follows:

Formulation 2

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions

Suspensions each containing 0.1–1000 mg of medicament per 5 mL dose are made as follows:

Formulation 3

| Ingredient | Quantity (amount/5 mL) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water | qs to 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

A particular advantage of the compounds of formula I when used in lowering serum cholesterol levels is the fact that they evoke only modest uterotrophic activity, as identified by a) only slight gains in uterine weight and b) lack of increase in the number of eosinophils observed in the stromal layer of ovariectomized rats.

The following nonlimiting test examples illustrate the methods of this invention.

Test Procedures

Seventy-five day old female Sprague Dawley rats (weight range of 200 to 225 g) were obtained from Charles River Laboratories (Portage, Mi.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen/Tissue Collection

After a one week acclimation period (therefore, two weeks post-OVX) daily dosing with test compound was initiated. All compounds were administered orally at 1 ml/kg body weight unless otherwise stated. 17α-ethynyl estradiol and the test compound were given orally as a suspension in 1% carboxymethylcellulose or 20% cyclodextrin. Animals were dosed daily for 4 days. Following the dosing regimen animals were weighed and anesthetized with a ketamine: Xylazine (2:1, V:V) mixture, and a blood sample was collected by cardiac puncture. Each animal was then sacrificed by asphyxiation with CO2; the uterus was removed through a midline incision and a wet weight was determined.

Cholestrol Analysis

Blood samples were allowed to clot at room temperature for 2 hrs, and serum was obtained following centrifugation for 10 min at 3000 rpm. Serum cholesterol was determined using a Boehringer Mannheim Diagnostics high performance cholesterol assay. Briefly, the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay

Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosinophils in the uterus is an indication of estrogenic activity of a compound. The maximal velocity of a 15 second interval was determined over the initial, linear portion of the reaction curve.

Sources of Compounds

17α-ethynyl estradiol was obtained from Sigma Chemical Co., St. Louis, Mo.

Experimental Groups

All experimental groups were comprised of five or six animals.

Figure 1:
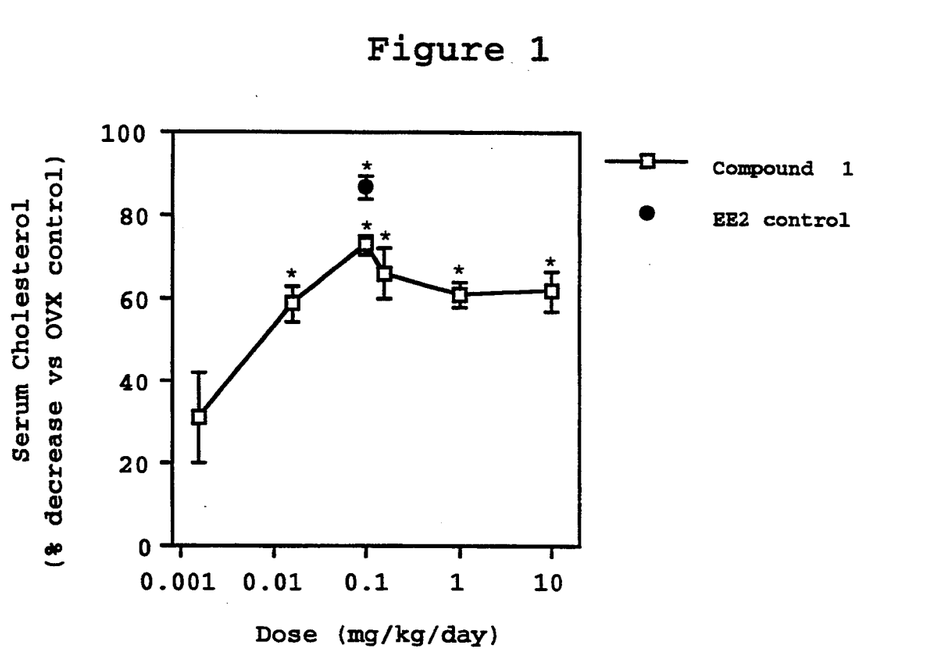
FIG. 1 is a summary of the effect of 2-[4-[2-(1-piperidino)ethoxy]phenyl]-3-(4-hydroxyphenyl)-7-hydroxy-2H-1-benzopyran (Compound 1) on serum cholesterol in rats, using the procedure described in the examples infra. The effect of the control, ethynyl estradiol (EE2), is shown for comparison.
Figure 2:
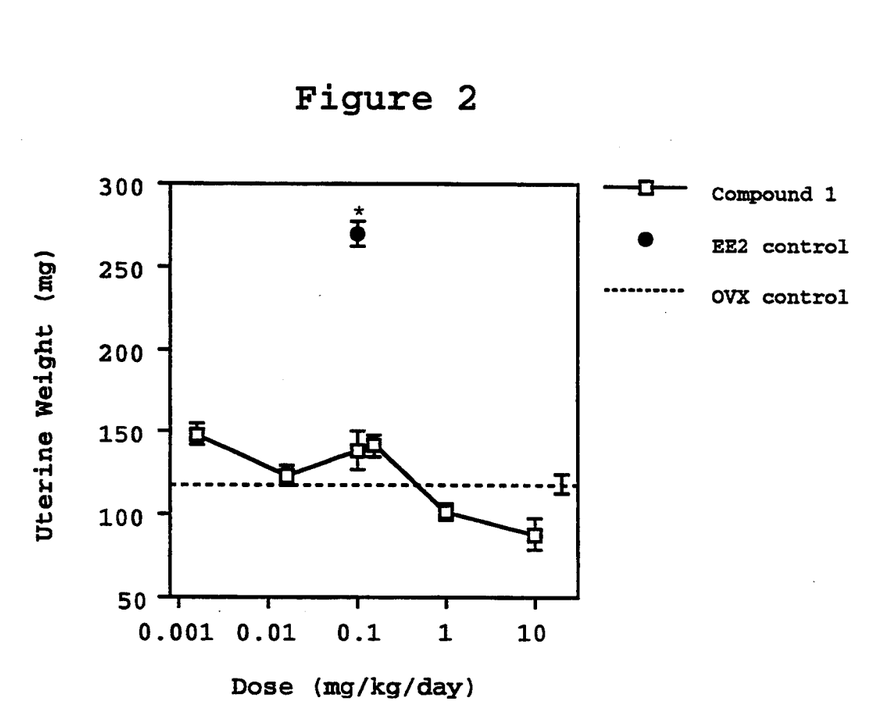
FIG. 2 compares the effects of Compound 1 on uterine weight in rats, the ovariectomized control animals (OVX) and the EE2 control animals, using the test system described in the examples infra.
Figure 3:
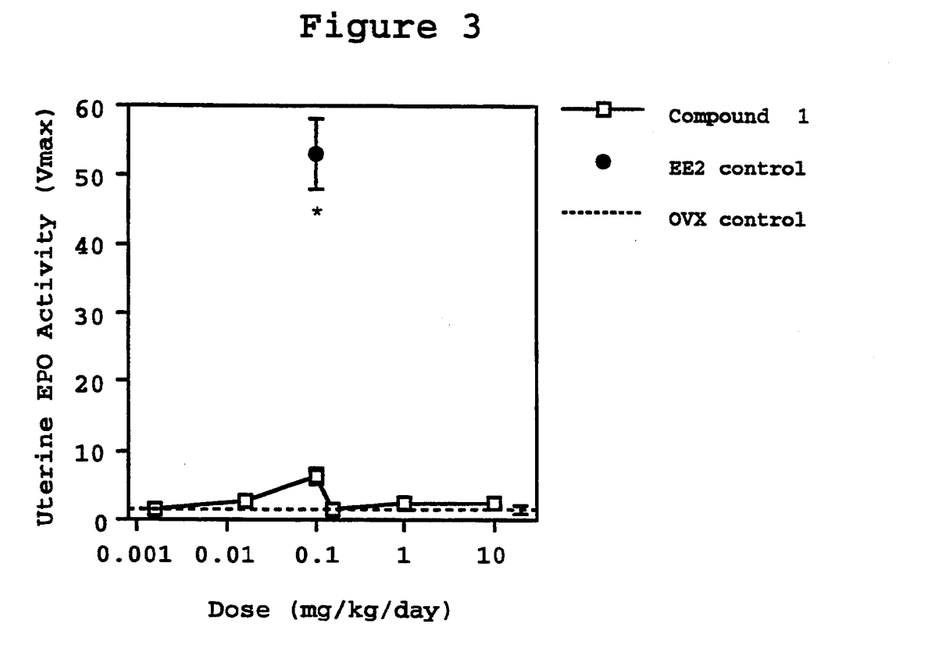
FIG. 3 shows the effect of Compound 1 on uterine eosinophil peroxidase levels, again comparing it with OVX and EE2 controls, using the test system described in the examples infra.

The results of the studies are presented in FIGS. 1-3. In summary, ovariectomy of the rats caused an increase in serum cholesterol as compared to intact vehicle treated controls. Estrogen, administered in the orally active form of ethynyl estradiol (EE2), causes a decrease in serum cholesterol in a dose dependent manner, but it also exerts a stimulatory action on the uterus, resulting in uterine weights approaching that of an intact rat when administered at 100 μg/kg/day. Results are reported as the mean of measurements from 5 to 6 rats±the standard error of the mean.

In these studies, Compound 1 also caused a serum cholesterol decrease in a dose dependent manner; however, only minimal increase of uterine weight over the ovariectomized controls was present in these animals. The serum cholesterol effects of Compound 1 are represented in FIG. 1.

FIG. 2 compares the effect on uterine weight gain of Compound 1 and EE2 versus ovariectomized controls. As FIG. 2 shows, rats treated with Compound 1 had uterine weights similar to those of ovariectomized controls and much less than those of the EE2-treated rats.

Increases in uterine eosinophils are a sign of estrogenicity of therapeutic agents and may be associated with increased incidence of uterine cancer. When Compound 1 was administered as described supra, there was no statistically measurable increase in uterine eosinophil peroxidase activity over the ovariectomized controls. This result was in contrast to the results seen with estrogen (EE2), as shown in FIG. 3.

We claim:

1. A method of lowering serum cholesterol levels, comprising administering an effective amount of a compound of formula (I):

wherein:
$R^1$ and $R^2$ are, independently, —H, —OH, halo, —$OC_1$-$C_{17}$ alkyl, —$OC_3$-$C_6$ cycloalkyl, —O(-CO)$C_1$-$C_{17}$ alkyl, —O(CO) aryl, —O(CO)O aryl, or —$OSO_2$-(n-butyl or n-pentyl);

$R^3$ and $R^4$ is —H, methyl, ethyl, propyl, ethenyl or ethynyl; or a pharmaceutically acceptable salt or solvate thereof, to an animal in need of lower cholesterol levels.

2. A method according to claim 1 wherein $R^4$ is H.

3. A method according to claim 1 wherein $R^4$ is methyl, ethyl or propyl.

4. A method according to claim 3 wherein $R^4$ is methyl.

5. A method of claim 2 wherein $R^1$ and $R^2$ are each independently H, OH, or $C_{1-4}$ alkoxy.

6. A method of claim 4 wherein $R^1$ and $R^2$ are each independently H, OH, or $C_{1-4}$ alkoxy.

7. A method of claim 2 wherein $R^1$ is H.

8. A method of claim 4 wherein $R^1$ is H.

9. A method of claim 7 wherein $R^2$ is hydroxy.

10. A method of claim 8 wherein R2 is hydroxy.

11. A method of claim 5 wherein $R^3$ is:

12. A method of claim 6 wherein $R^3$ is:

13. A method of claim 9 wherein $R^3$ is:

14. A method of claim 10 wherein $R^3$ is:

15. The method according to claim 1 wherein the said compound is 2-[4-[2-(1-piperidino)ethoxy]phenyl]-3-(4-hydroxyphenyl) -7 -hydroxy-2H-1-benzopyran, 2-[4-[2-(1-piperidino) ethoxy]phenyl]-3-(4-hydroxyphenyl) -2H-1-benzopyran, 2-[4-[2-(1-piperidino)ethoxy]-phenyl]-3-phenyl-7-methoxy-2H-1-benzopyran, 2-[4-[2-(1-pyrrolidino) ethoxy]phenyl]-3-(4-hydroxyphenyl)-7-methoxy-2H-1-benzopyran or 2-[4-[2-(1-piperidino)ethoxy]phenyl]-3-(4-hydroxyphenyl)-4-methyl-7-hydroxy-2H-1-benzopyran.

16. A method of claim 1 wherein the animal is a human.

17. A method of claim 16 wherein the human is a female.

18. A method of claim 17 wherein the female is estrogen deficient.

19. A method of claim 18 wherein the female is postmenopausal.

* * * * *